United States Patent [19]

Imada et al.

[11] Patent Number: 4,818,441
[45] Date of Patent: Apr. 4, 1989

[54] QUININE DERIVATINES

[75] Inventors: Isuke Imada, Izumi; Shinji Terao, Toyonaka; Mitsuru Kawada, Amagasaki; Mitsuru Shiraishi, Suita, all of Japan

[73] Assignee: Takeda Chemical Industries, Ltd., Osaka, Japan

[21] Appl. No.: 165,009

[22] Filed: Jul. 1, 1980

[30] Foreign Application Priority Data

Jul. 2, 1979 [JP] Japan ................. 54-84291

[51] Int. Cl.⁴ .............. C07C 50/02; C07C 50/26
[52] U.S. Cl. ..................................... 260/396 R
[58] Field of Search ..................... 260/396 R

[56] References Cited

U.S. PATENT DOCUMENTS 3,728,363 4/1973 Morimoto et al. ............ 260/396 R
3,849,453 11/1974 Morimoto et al. ............ 260/396 R
3,957,836 5/1976 Morimoto et al. ............ 260/396 R
4,139,545 2/1979 Morimoto et al. ............ 260/396 R

OTHER PUBLICATIONS

J. Weichet et al., Chemical Abstracts, vol. 65:13771d, 1966.
Creed, David, et al., Journal American Chemical Society, 93:2, Jan. 27, 1971, pp. 502-505, and 508-510.
Imada et al., Biochemistry, vol. 9, No. 14, 1970, 2870-2878.

Primary Examiner—Werren B. Lone
Attorney, Agent, or Firm—Wenderoth, Lind & Ponack

[57] ABSTRACT

A compound of the general formula:

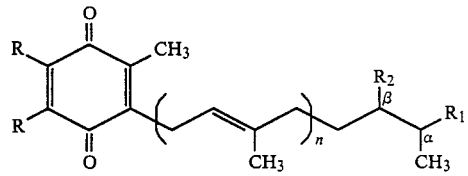

wherein $\alpha \mathrel{\text{---}} \beta$ means a saturated bond or a double bond; each R independently of one another is a methyl group or a methoxy group, or two R's taken together represent a group of $-CH=CH-CH=CH-$; n is zero or an integer of 1 through 9; when $\alpha\mathrel{\text{---}}\beta$ is a saturated bond, $R_2$ is a hydrogen atom or hydroxyl group, and when $\alpha\mathrel{\text{---}}\beta$ is a double bond, $R_2$ is a hydrogen atom; when $\alpha\mathrel{\text{---}}\beta$ is a double bond or when $R_2$ is a hydroxyl group, $R_1$ is a carboxyl group, a group of $-(CH_2)_m-OH$ (wherein m is an integer of 1 through 3) or a group of

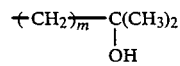

(wherein m is an integer of 1 through 3); when $\alpha \mathrel{\text{---}} \beta$ is a saturated bond and $R^2$ is a hydrogen atom, $R_1$ is a hydroxymethyl group or a group of

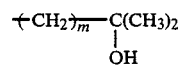

(wherein m is an integer of 1 through 3) has pharmacological actions such as membrane stabilizing activity (e.g. lysosomal membrane stabilizing activity), mitochondrial electron transport activity, hypotensive activity, activity to inhibit cardiac hypertrophy, tracheal muscle relaxant activity, cerebral circulation improving activity and cerebral ischemia preventive activity and is of value in the prophylaxis and treatment of hypertension, cardiac failure, asthma, cerebral apoplexy and other diseases, as a cardiac failure remedy, bronchodilator, cerebral circulation improving agent or the like.

14 Claims, No Drawings

QUININE DERIVATINES

This invention relates to novel quinone compounds which are of value as medicines or intermediates thereof and a method of producing said quinone compounds.

The fat-soluble vitamins, such as α-tocopherol, phylloquinone, ubiquinone, etc., are known to stabilize the biological membranes as one of their physiological properties and have been reported to produce various clinical and therapeutic effects. Thus, these are compounds of value as medicines. However, because of their generally high fat-solublity, these vitamins present several problems in connection with administration and onset of action. The research undertaken by the present inventors for developing derivatives free from the above-mentioned disadvantages led to the discovery of certain compounds which are relatively sparingly soluble in fats and have excellent physiological activities. The present invention is based on this discovery.

Accordingly this invention relates to:

1. A compound of the general formula:

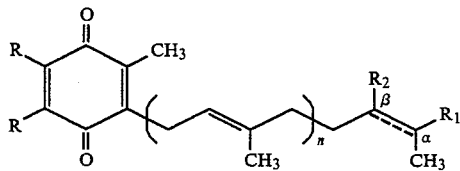

wherein $\alpha$====$\beta$ means a saturated bond or a double bond; each R independently of one another is a methyl group or a methoxy group, or two R's taken together represent a group of —CH=CH—CH=CH—; n is zero or an integer of 1 through 9; when $\alpha$===$\beta$ is a saturated bond, $R_2$ is a hydrogen atom or hydroxyl group, and when $\alpha$===$\beta$ is a double bond, $R_2$ is a hydrogen atom; when $\alpha$===$\beta$ is a double bond or when $R_2$ is a hydroxyl group, $R_1$ is a carboxyl group, a group of —(CH$_2$)$_m$OH (wherein m is an integer of 1 through 3) or a group of

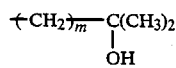

(wherein m is an integer of 1 through 3); when $\alpha$===$\beta$ is a saturated bond and $R_2$ is a hydrogen atom, $R_1$ is a hydroxymethyl group or a group of

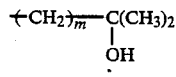

(wherein m is an integer of 1 through 3).

2. A compound of 1 wherein $\alpha$====$\beta$ means a double bond, $R_1$ is a carboxyl group and $R_2$ is a hydrogen atom;

3. compounds of 1 wherein $\alpha$====$\beta$ is a saturated bond, $R_1$ is a carboxyl group and $R_2$ is a hydroxyl group;

4. compounds of 2 or 3 wherein n is equal to zero;

5. compounds of 1 wherein $\alpha$====$\beta$ is a double bond, $R_1$ is a group of —(CH$_2$)$_m$OH (where m is an integer of 1 through 3) and $R_2$ is a hydrogen atom;

6. compounds of 5 wherein m is equal to 3;

7. compounds of 6 wherein n is zero or an integer of 1 through 6;

8. compounds of 7 wherein n is zero or an integer of 1 through 2;

9. compounds of 5 wherein n is an integer of 1 through 9 and m is equal to 1;

10. compounds of 1 wherein $\alpha$====$\beta$ is a saturated bond, $R_1$ is —CH$_2$OH and $R_2$ is a hydrogen atom;

11. compounds of 10 wherein n is equal to zero;

12. compounds of 1 wherein $\alpha$====$\beta$ is a double bond, $R_1$ is a group of

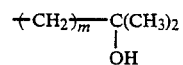

(where m is an integer of 1 through 3) and $R_2$ is a hydrogen atom;

13. compounds of 12 wherein m is 2 or 3;

14. compounds of any of 1 through 13 wherein R is a methoxy group.

The quinone compounds of the above general formula (I), when taken into the body, are in intertransformable relation with hydroquinones of the general formula:

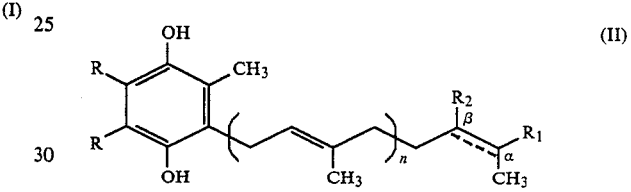

(wherein each of the symbols is as previously defined) and are equivalent to the latter as chemical compounds and in the physiological sense. That is, compound (I) and compound (II) are partly converted to each other in the living body by the action of reductase or oxidase.

The quinone compound (I) according to this invention is produced, for example by oxidizing a compound of the general formula:

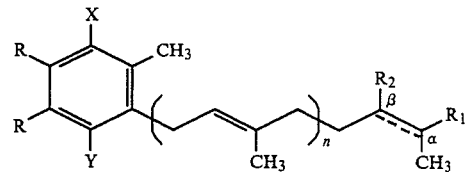

[wherein X and Y may be the same or different and each means a hydroxyl or amino group which may optionally be protected, provided that one or the other of X and Y may be a hydrogen atom; $\alpha$ === $\beta$, R, $R_1$, $R_2$ and n are as defined above.]

The protective group, if any, on said hydroxyl group may be any of the protective groups hitherto known, only if it is capable of protecting the hydroxyl group. By way of example, there may be mentioned $C_1$ to $C_4$ alkyls (e.g. methyl, ethyl), $C_1$ to $C_4$ alkoxymethyl (e.g. methoxymethyl, ethoxymethyl), aralkyls (e.g. benzyl, p-nitrobenzyl, p-methoxybenzyl), acyls (e.g. alkanoyls up to 4 carbon atoms, e.g. acetyl, propionyl, benzoyl, p-nitrobenzoyl, phenylacetyl), tetrahydropyranyl, tetrahydrofuranyl, etc. Preferred are methoxymethyl, benzyl, acetyl, tetrahydropyranyl, tetrahydrofuranyl, etc.

As examples of the protective group, if any, on said amino group, there may be mentioned acyl groups [such as alkanoyls up to 4 carbon atoms (e.g. acetyl, propionyl, etc), benzoyl, p-nitrobenzoyl, phenylacetyl], aralkyls (e.g. benzyl, p-nitrobenzyl, p-methoxybenzyl) and so on.

When the hydroxyl or/and amino groups X and Y are protected, it may be desirable, depending on the type of protective group present, to carry out a deprotecting reaction. For this deprotecting reaction, a per se known reaction suited to the particular protective group is employed (e.g. hydrolysis, catalytic reduction). When the protective group is alkyl, aralkyl, alkoxymethyl, acyl, tetrahydropyranyl or tetrahydrofuranyl, the desired cleavage of the protective group can be effected by hydrolysis in the presence of an acid (e.g. hydrochloric acid, sulfuric acid, perchloric acid) or a base (e.g. sodium hydroxide, potassium hydroxide, sodium carbonate, potassium carbonate, etc.) When the protective group is aralkyl or acyl, it can also be removed under reductive conditions. Thus, when the protective group is benzyl, for instance, it can be removed by catalytic reduction or by reduction in the presence of an alkali or alkaline earth metal and an amine solvent. When the protective group is an acyl group, it can be removed by reduction with a metal hydride, e.g. lithium aluminum hydride, or by hydrolysis under reductive conditions.

The starting compound of general formula (III) is first subjected, if necessary, to the above deprotecting reaction and, then, subjected to the oxidation reaction to obtain the desired quinone compound (I). When the compound (III) is one in which both X and Y are hydroxyl, or one in which one of X and Y is hydroxyl with the other being an amino group which may optionally be protected, the oxidation reaction may be carried out by, for example, ferric chloride oxidation, atmospheric oxidation, silver oxide oxidation, etc. Depending on the type of protective group on the starting compound (III), the deprotecting reaction and oxidation reaction, of course, take place simultaneously. For example, when the hydroxyl-protecting group is methyl or methoxymethyl, the desired compound of general formula (I) can be obtained in a single step by permitting silver (II) oxide (AgO) to act oxidatively on (III) under acidic conditions (e.g. in the presence of nitric acid). When one of X and Y in general formula (III) is a hydroxyl group which may optionally be protected, the other being a hydrogen atom, desirable oxidation reactions include those involving the use of potassium nitro-sodisulfonate (Fremy's salt), cobalt complex/oxygen, hydrogen peroxide, an organic peroxide and the like. Of course, in this case, too, the deprotection and oxidation reactions take place simultaneously depending on the type of protective group on the starting compound.

As the solvent used in this reaction there may be mentioned water, dioxane, acetone, tetrahydrofuran, lower alcohols (e.g. methanol, ethanol), organic acids (e.g. acetic acid), inorganic acids (e.g. hydrochloric acid, nitric acid), halogenated hydrocarbons (e.g. dichloroethane), dimethylformamide, hexamethylphosphoric triamide, etc. as well as various mixtures thereof. Of course, solvents which make for a sufficient contact of the starting material with the oxidizing agent are preferred. Depending on the stability of starting compound, a buffered aqueous solution or a solvent containing an acid or base is employed.

The quinone compound (I) produced in the above manner can be isolated from the reaction mixture by per se known separation-purification procedures (e.g. recrystallization, column chromatography, thin layer chromatography, high performance liquid chromatography). Where the quinone compound (I) contains a group or groups capable of forming salts (e.g. COOH, OH), the compound (I) may be converted to salts such as alkali metal salts (e.g. sodium and potassium salts) by per se known procedures and isolated as such. Of course, such salts also fall within the scope of this invention.

The starting compound of general formula (III) can be prepared by any of per se known methods or a modified version thereof. Some typical production routes are shown below.

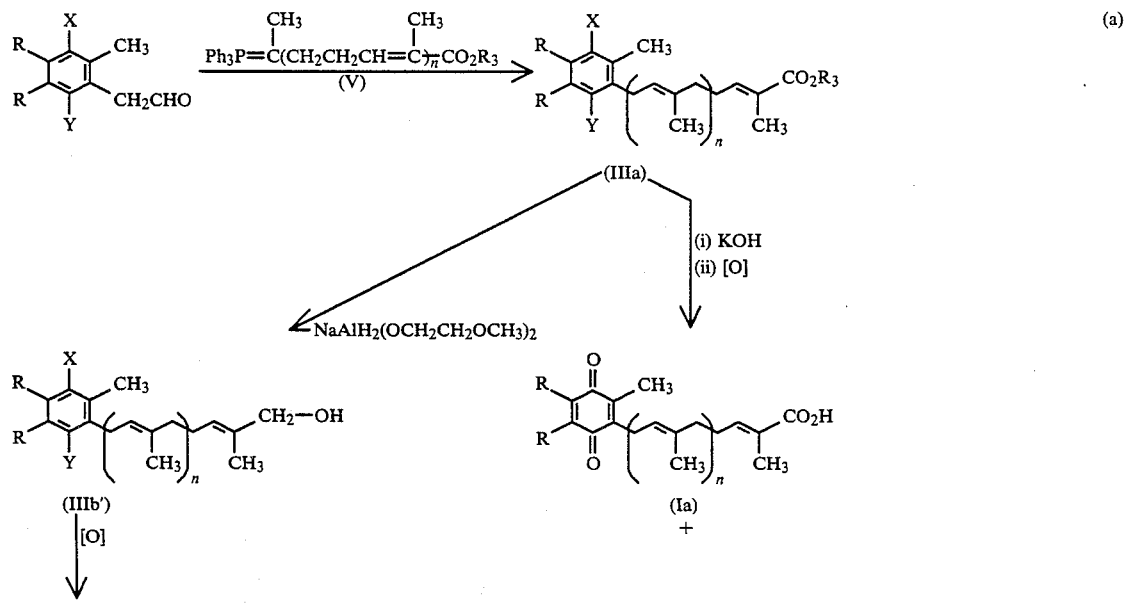

-continued
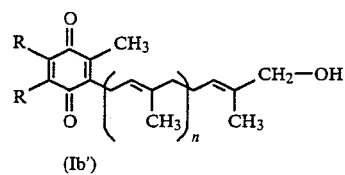
(Ib')
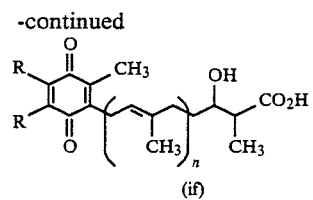
(If)
(b)
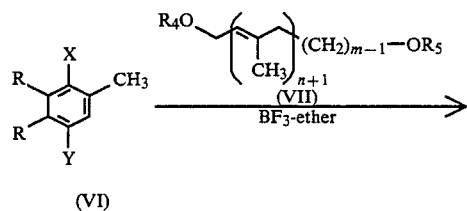
(VI) → (IIIb)
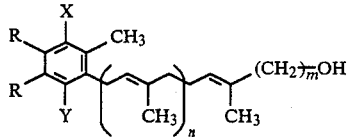
[O]
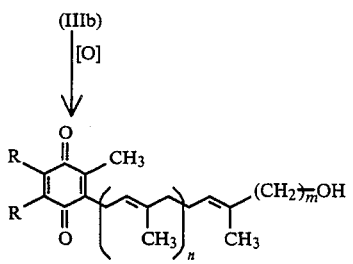
(Ib)
(c)
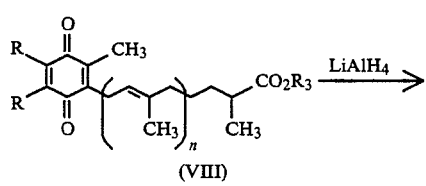
(VIII) →LiAlH₄→
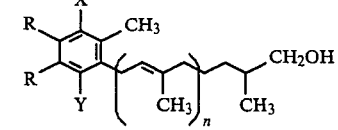
(IIIe)
[O]
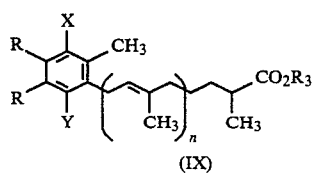
(IX) →LiAlH₄→
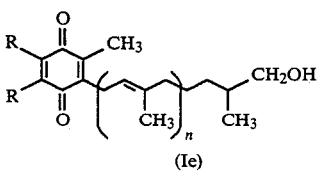
(Ie)
(d)
(VI) →(X)/BF₃·ether→
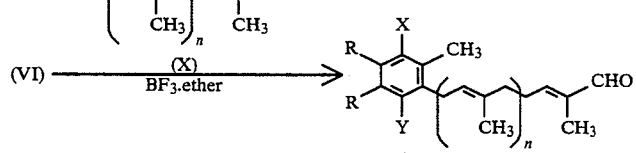
(IIIc)
[O]
((IIIb') ←NaBH₄— 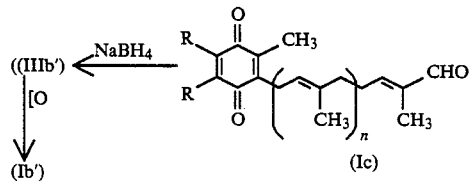 ←NaBH₄—
[O]↓
(Ib')
(Ic)

(e)
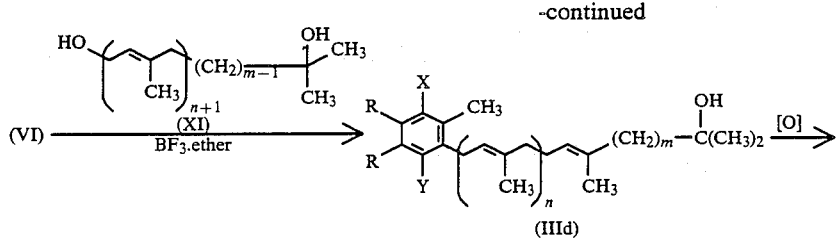
(IIId)
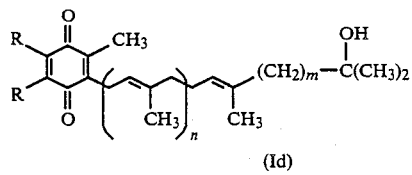
(Id)
(f)
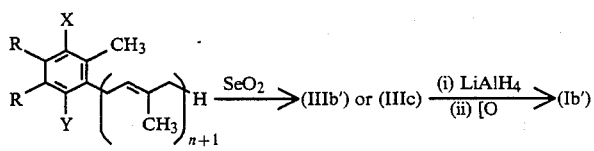
(g)
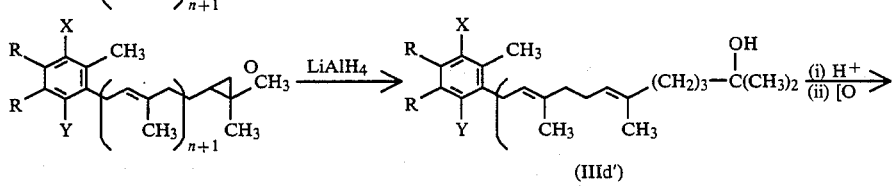
(IIId')
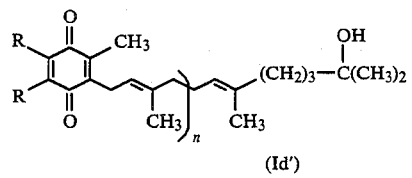
(Id')
(h)
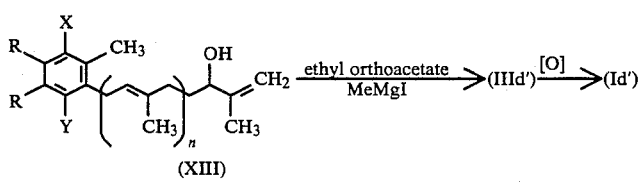
(XIII)
(i)
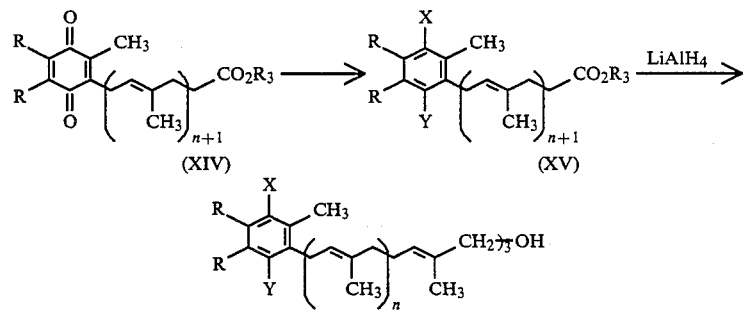
(XIV) (XV)
(IIIb'')
(j)
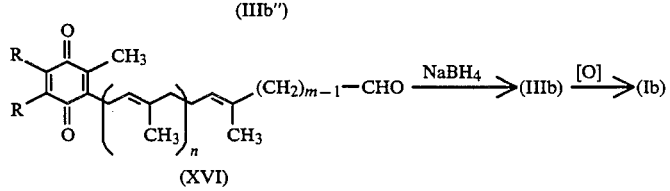
(XVI)
In the above formulas, $R_3$ is a lower alkyl group (e.g. methyl, ethyl); $R_4$ and $R_5$ respectively mean a hydrogen atom or a tetrahydropyranyl or tetrahydrofuranyl group; and the other symbols are as defined hereinbefore.

The compound of general formula (I) according to this invention displays a biological membrane stabilizing effect which is one of the known physiological activities of the fat-soluble vitamins mentioned hereinbefore. Thus, for example, when using a rat liver lysosomal membrane as a biological membrane specimen, the action of compound (I) to inhibit a thermal denaturation thereof was investigated, and the compound (I) was found to display a pronounced inhibitory effect as compared with said fat-soluble vitamins, this attesting to its potent activity to stabilize the lysosomal membrane.

Since lysosomal membrane-stabilizing activity is developed through adenosine-2′,3′-cyclic monophosphate (c-AMP) of tissue cells, the action of compound (I) on c-AMP phosphodiesterase, the c-AMP decomposing enzyme, was investigated. As shown in Table 1, this compound (I) was found to display a marked inhibitory action. Therefore, it was confirmed, if only from this fact, that the compound according to this invention has a membrane-stabilizing activity. The activity of the compound (I) was even superior to that of theophylline which is known to have a potent activity of this kind.

TABLE 1

The lysosomal membrane stabilizing activity and phosphodiesterase inhibitory activity of compounds of this invention

| Compound | R | Action on lysosome[1] Concentration (M) | % Inhibition on release of $\beta$-Glucuronidase (%) | % Inhibition on release of acid phosphatase (%) | Action on phosphodiesterase[2] Concentration (mM) | % Inhibition (%) |
|---|---|---|---|---|---|---|
| Compound 1 (quinone with OH, COOH, CH₃ substituents) | $H_3CO$ | $2 \times 10^{-4}$ | 18 | 49 | 1 | 60 |
| | $H_3C$ | $2 \times 10^{-4}$ | 29 | 48 | 1 | 20 |
| | cyclo | $2 \times 10^{-4}$ | 15 | 35 | 1 | 40 |
| Compound 2 (quinone with CH₃, COOH, CH₃ substituents) | $H_3CO$ | $2 \times 10^{-4}$ | | | 1 | 47 |
| | $H_3C$ | $2 \times 10^{-4}$ | 36 | 44 | 1 | 42 |
| | cyclo | $2 \times 10^{-4}$ | 36 | 40 | 1 | 86 |
| Compound 3 (quinone with CH₃, OH, CH₃ substituents) | $H_3C$ | $2 \times 10^{-4}$ | 37 | 32 | 1 | 41 |
| | cyclo | $2 \times 10^{-4}$ | 37 | 39 | 1 | 55 |
| Compound 4 (quinone with CH₃ chain, OH, CH₃) | $H_3CO$ | $2 \times 10^{-4}$ | 28 | 37 | 1 | 84 |
| | $H_3C$ | $2 \times 10^{-5}$ | 23 | 34 | | |
| | cyclo | $2 \times 10^{-5}$ | 25 | 36 | 1 | 53 |
| Compound 5 (quinone with CH₃ chain, OH, CH₃) | $H_3CO$ | $2 \times 10^{-4}$ | 38 | 43 | 1 | 38 |
| | $H_3C$ | $2 \times 10^{-4}$ | 29 | 21 | 1 | 44 |
| Compound 6 (quinone with longer chain, CH₃, CH₃, OH, CH₃) | $H_3C$ | $2 \times 10^{-4}$ | 20 | 16 | 1 | 18 |
| | cyclo | $2 \times 10^{-5}$ | 18 | 9 | 1 | 29 |
| theophylline[3] | | | | | 1 | 32 |

(1) Rat liver lysosome was incubated at 37° C. for 90 minutes and the activities of $\beta$-glucuronidase and acid phosphatase released from the lysosome due to instabilization of the membrane during that time were assayed and compared with the results obtained in the absence of the test compound. The test compound was added as dissolved in dimethylformamide.

(2) The rate of decomposition of adenosine-2′,3′-cyclic phosphate by beef heart muscle phosphodiesterase was compared with the rate found in the absence of the test compound.

(3) Commercial phosphodiesterase inhibitor

Among the compounds (I) of this invention, the compounds in which R is methoxy displayed is marked degree of mitochondrial electron transport activity which is an activity known to be possessed in common by ubiquinone compounds. Thus, the compound of this invention was added to a ubiquinone-deficient enzyme preparation made from beef heart mitochondria and the electron transport activity was investigated by assaying the succinate oxidase activity. The result, presented in Table 2, shows a marked degree of activity.

TABLE 2

Electron transport activity of the compound of this invention*

| Compound | Level of addition (n mole) | Succinate oxidase activity** [oxygen consumption (n atoms oxygen) min. per mg protein] |
|---|---|---|
| Control | 0 | 7.1 ± 2.8 |
| A*** ⟶⟶⟶OH (CH₃, CH₃) | 5 | 42.4 ± 6.3 |
| A ⟶⟶⟶OH (CH₃, CH₃) | 5 | 35.5 ± 3.5 |
| A ⟶⟶OH (CH₃) | 5 | 18.2 |
| A ⟶OH (CH₃) | 5 | 12.5 |
| A ⟶⟶ (CH₃, CH₃, CH₃, CH₃) | 5 | 21.4 |

*The ubiquinone-deficient enzyme preparation was prepared from beef heart mitochondria in accordance with the method of Lester and Fleischer (Biochem. Biophys. Acta, 47, 358, 1961). The electron transport activity was investigated by assaying the succinate oxidase activity.
**The composition of the reaction system (2 ml) was as follows. 0.2 M sucrose, 10 mM Tris-HCl (pH 7.4), 20 mM KCl, 3 mM MgCl₂, 50 mM EDTA 2Na, enzyme protein 1.99 mg, 50 μM potassium succinate, cytochrome C 0.2 mg. 1% Nikkol OP-10 (produced by Nikko Chemicals Co. Ltd.) 5 μl (control group) or 5 μl of a 1 mM solution of the test compound in 1% Nikkol OP-10. The oxygen consumption of this solution was measured with an oxygen electrode device (Gilson Medical Electronics' Inc.).

***A: 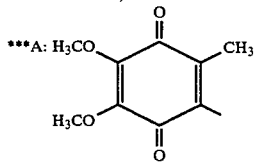

The compounds of general formula (I) wherein R is methoxy further showed hypotensive activity and activity to inhibit cardiac hypertrophy due to aging. Thus, 21-week rats with spontaneous hypertension (Ta:SHR) were organized into groups of 8 to 10 individuals each, and one of the present compounds, i.e. 6-(6-hydroxy-3-methyl-3-hexenyl)-2,3-dimethoxy-5-methyl-1,4-benzoquinone (formula (I) wherein R:H₃CO, n:O, R₂:H, R₁:(CH₂)₃OH, α====β:double bond), and, as controls, ubiquinone homologs (ubiquinone-7 and ubiquinone-10) were each administered by oral gavage in doses of 10 mg/kg/day for 2 weeks (except on Sunday) or administered as incorporated in feed at the rate of 6 to 16 mg/kg/day for 4 weeks. Blood pressures were measured every week, and as for the oral gavage administration group, the blood was withdrawn from the abdominal aorta at the end of the administration period while each animal was kept under anesthesia with pentobarbital sodium (30 mg/kg, intraperitoneal). Then, the kidneys, liver, heart and adrenals were enucleated and weighed. At two weeks in the case of the oral gavage administration group (Table 3) or during week-1 through week-4 in the case of the feed incorporation group (Table 4), antihypertensive effects were observed. In the oral gavage administration group, the organ weights taken at the end of said administration period showed a significant decrease of weight of the heart in the group dosed with the present compound as compared with the control group, although other organs did not show such decreases (Table 5). Since it is generally acknowledged that, in the case of ubiquinone homologs, such hypotensive effects are attributable to a depression of the ubiquinone (Q) deficiency in mitochondria, the degree of Q deficiency of heart mitochondria was investigated in 6 cases showing blood pressures over 230 mmHg in the control group and 6 cases showing blood pressures under 212 mmHg in the group dosed with the present compound.

In accordance with the method of G. P. Littaru et al. (Int. J. Vitam. Nutr. Res., 42, p. 291, 1972), heart mitochondria were separated and in accordance with the method of Ziegler and Rieske (Methods in Enzymology, Vol. 10, p. 231, 1967), the Q deficiency of heart mitochonidria was determined. The results, presented in Table 6, shows a depression of the degree of Q deficiency in the group dosed with the present compound.

TABLE 3

Effect of drugs on the blood pressure of Ta: SHR (10 mg/kg/day, administered by oral gavage)

| Group (No. of individuals) | No. of weeks following medication | | |
|---|---|---|---|
| | 0 | 1 | 2 |
| Control (10) | 200 ± 13[1] | 203 ± 9 | 212 ± 11 |
| Group dosed with the present compound (8) | 200 ± 14 | 206 ± 8 | 204 ± 11 |
| Ubiquinone-7 group (9) | 199 ± 9 | 204 ± 9 | 206 ± 11 |

[1]Blood pressure: mmHg Mean ± standard error

TABLE 4

Effect of drugs on the blood pressure of Ta: SHR (6-16 mg/kg/day, administered as incorporated in feed)

| Group | (No. of individuals) | No. of weeks following medication | | | | |
|---|---|---|---|---|---|---|
| | | 0 | 1 | 2 | 3 | 4 |
| Control | (10) | 205 ± 12[1] | 198 ± 11 | 202 ± 9 | 194 ± 13 | 205 ± 12 |
| Present compound | (10) | 206 ± 15 | 193 ± 15 | 190 ± 15 | 178 ± *18[2] | 193 ± 25 |
| Ubiquinone-10 | (10) | 206 ± 16 | 191 ± 14 | 187 ± 10** | 199 ± 17 | 205 ± 13 |

[1]Blood pressure: mmHg. Mean ± standard error
[2]Student's t-test, *p < 0.05, ** P < 0.1

TABLE 5

Effect of consecutive administration of the compound of this invention on the organ weights of Ta: SHR (10 mg/kg/day, oral gavage)

| Group | (No. of individuals) | Kidney (g) | Liver (g) | Heart (g) | Adrenal (mg) |
|---|---|---|---|---|---|
| Control | (10) | 2.57 ± 0.17 | 13.00 ± 0.73 | 1.59 ± 0.14 | 51.6 ± 3.6 |
| Present compound | (8) | 2.40 ± 0.33 | 13.56 ± 1.96 | 1.42 ± 0.15* | 50.4 ± 6.6 |

*$P < 0.05$

TABLE 6

Effect of the compound of this invention on the degree of ubiquinone deficiency of Ta: SHR heart mitochondria at the end of consecutive administration (10 mg/kg/day, oral gavage)

| Group | (No. of individuals) | Succinate dehydrogenase - Q reductase system | | |
|---|---|---|---|---|
| | | Specific activity | Specific activity in the presence of Q-2 | % Ubiquinone deficiency |
| Control | (6) | 0.539 ± 0.067 | 0.809 ± 0.104 | 33.15 ± 1.09 |
| Present compound | (6) | 0.499 ± 0.044 | 0.656 ± 0.053 | 24.6 ± 1.2*** |

***$P < 0.001$

The compound according to this invention further displayed tracheal muscle relaxant activity. Thus, the isolated guinea pig trachea was cut into a strip in accordance with the method of Kiyomoto et al. [Yamaura Y. ed. "Zensoku (Asthma)", Kodansha, Tokyo, p. 152, 1974 (Japanese language)], set up in a Magnus device and kept at constant contraction with potassium chloride solution five times the concentration of Tyrode solution. Under the above conditions, a solution of the drug in DMF was added and the muscle relaxant effect was recorded on a kymograph. The results, presented in Table 7, show that the compound according to this invention has a tracheal muscle relaxant action.

TABLE 7

Tracheal Muscle Relaxant Activity of the compound of this invention

| Compound | Concentration (g/ml) | Tracheal muscle relaxant action[1] (%) |
|---|---|---|
| R: H₃CO | $3 \times 10^{-5}$ | 85.5 |
| | $10^{-4}$ | 100 |
| R: H₃C | $3 \times 10^{-5}$ | 67 |
| | $10^{-4}$ | 100 |
| Theophylline[2] | $3 \times 10^{-5}$ | 60.4 |
| | $10^{-4}$ | 93 |

[1] With the relaxant effect of noradrenaline being taken as 100.
[2] Commercial bronchodilator To determine the toxicity of the compound according to this invention, each of the compounds indicated below was orally administered to mice in groups of 4 individuals at a dose of 300 mg/kg body weight. The administration resulted in no death at all.

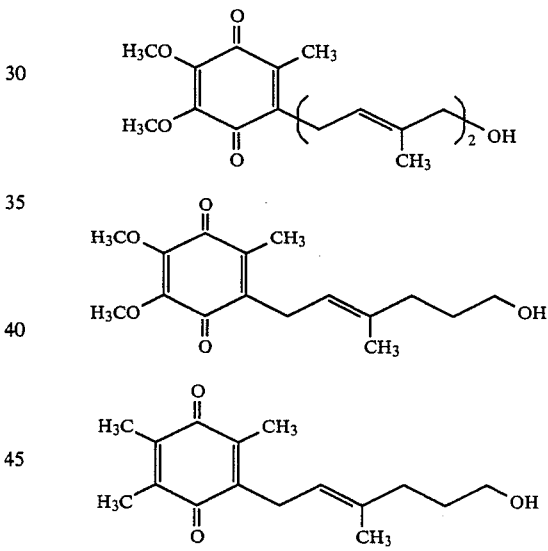

As described hereinbefore, the compound (I) according to this invention has pharmacological activities such as membrane stabilizing activity (e.g. lysosomal membrane stabilizing activity), mitochondrial electron transport activity, hypotensive activity, activity to inhibit cardiac hypertrophy, tracheal muscle relaxant activity, cerebral circulation improving activity and cerebral ischemia preventive activity in mammalian animals (e.g. rat, mouse, guinea pig, rabbit, cattle and man) and, as such, is of value in the prophylaxis and treatment of hypertension, cardiac failure, asthma, cerebral apoplexy and other diseases, as cardiac failure remedy, bronchodilator, cerebral circulation improving agent or the like.

The compound (I) according to this invention has some additional beneficial features which are desirable in medicines, such as low toxicity, low fat-solubility and fast absorption.

Among the compounds (I) of this invention, the compounds in which R is methoxy are particularly desirable in terms of the above-mentioned pharmacological activities. Moreover, the compounds wherein α β is a double bond, $R_1$ is —$(CH_2)_mOH$ (m is an integer of 1 to 3 and preferably an integer equal to 3), $R_2$ is H, n=0 to 6 and preferably zero or an integer of 1 or 2 are especially suited for the purposes of this invention.

To use the compound (I) of this invention as one of the above-mentioned drugs, the compound (I), as such or in admixture with a per se known pharmaceutically acceptable carrier or excipient, can be administered safely by the oral route or otherwise, as such pharmaceutical compositions as tablets, granules, powders, capsules, injections, suppositories, etc. The said pharmactical compositions include medicinal preparations in various dosage forms. The proper dosage schedule varies with the condition of illness, administration route and other factors but when the compound (I) is orally administered as a therapeutic drug for hypertension or congestive heart failure, it is a suitable dosage schedule to use (I) at the rate of about 0.02 to 2 mg/kg body weight per dose, preferably about 0.2 to 0.8 mg/kg body weight per dose, approximately once to 3 times a day.

The compound (I) according to this invention is useful also as an intermediate for the production of various ubiquinone, menaquinone and tocopherylquinone derivatives.

The following reference and working examples are further illustrative but not limitative of this invention.

REFERENCE EXAMPLE 1

The compound VI (R=H$_3$CO, X=Y=OH) obtained by reducing 2,3-dimethoxy-5-methyl-1,4-benzoquinone (6.0 g) with Na$_2$S$_2$O$_4$ (60 g) in the conventional manner is dissolved in dioxane (60 ml), together with cinnamyl alcohol (6 g). To this solution is added BF$_3$-ether (25 g) at room temperature with stirring. The mixture is further stirred for 90 minutes, at the end of which time a solution of FeCl$_3$ (61 g) in 83% methanol (72 ml) is added. The reaction mixture is stirred for 10 minutes, after which cold water is added and extraction is carried out with ethyl acetate. The extract is worked up in the conventional manner and the residue is purified by column chromatography on silica gel (200 g) with CCl$_4$-ethyl acetate (10:1) as the eluent, followed by recrystallization from ethanol. The procedure provides orange-colored needles of 2,3-dimethoxy-5-methyl-6-(3'-phenyl-2'-propenyl)-1,4-benzoquinone. This product (3.9 g) is dissolved in acetic anhydride (80 ml) followed by addition of pyridine (20 ml) and then zinc (2 g) with stirring at room temperature. After 30 minutes' stirring, the insoluble matter is removed by filtering through celite, the filtrate is poured into cold water, and cold concentrated hydrochloric acid (20 ml) is added. The resultant precipitate is recrystallized from ethanol. By the above procedure are obtained colorless needles of 1,4-diacetoxy-2,3-dimethoxy-5-methyl-6-(3'-phenyl-2'-propenyl)benzene. This product (4.25 g) is dissolved in dioxane-water (3:1, 96 ml) and OsO$_4$ (38.1 mg) is added under stirring at room temperature. After 10 minutes' stirring, NaIO$_4$ (12.5 g) is added with stirring at room temperature. The mixture is further stirred for an hour, after which it is treated with cold water and extracted with ethyl acetate. The extract is worked up in the conventional manner and the residue is purified by column chromatography on silica gel (50 g) with CCl$_4$-acetone (10:1) as the eluent. The above procedure provides IV (R=H$_3$CO, X=Y=OCOCH$_3$) as colorless oil. To a 1.57 g portion of this product is added a solution of α-ethoxycarbonylethylidenetriphenylphosphorane (V) (n=O; R$_3$=C$_2$H$_5$; 2.0 g) in benzene (50 ml) and the mixture is heated under reflux for an hour. The reaction mixture is evaporated to dryness under reduced pressure and the residue is purified by column chromatography on silica gel (50 g) with CCl$_4$-ethyl acetate (5:1) as the eluent. The above procedure provides III$_a$ (R=H$_3$CO, X=Y=OCOCH$_3$, n=O, R$_3$=C$_2$H$_5$) as colorless oil.

REFERENCE EXAMPLE 2

To a solution of IIIa (R=H$_3$C, X=Y=OCOCH$_3$, n=O, R$_3$=C$_2$H$_5$) (203 mg) in benzene (20 ml) is added a 4% solution of NaAlH$_2$ (OCH$_2$CH$_2$OCH$_3$)$_2$ in benzene (15.9 ml) with stirring at room temperature. The mixture is stirred for 2 hours, at the end of which time cold water is added under stirring to thereby decompose the excess NaAlH$_2$(OCH$_2$CH$_2$OCH$_3$)$_2$. This reaction mixture contains III$_b$ (R=H$_3$C, X=Y=OH, m=1, n=O).

REFERENCE EXAMPLE 3

A solution of the reduced acetyl compound of ubiquinone-3 (580 mg) and SeO$_2$ (137 mg) in 95% ethanol (50 ml) is heated at 70°–80° C. for 6 hours, at the end of which time the reaction mixture is evaporated to dryness under reduced pressure. The residue is dissolved in CCl$_4$, the insoluble matter filtered off and the filtrate re-evaporated to dryness. The residue is purified by column chromatography on silica gel (30 g) with CCl$_4$-acetone (10:1) as the eluent, whereby III$_b$ (R=H$_3$CO, X=Y=OCOCH$_3$, n=2, m=1) is obtained as colorless oil.

REFERENCE EXAMPLE 4

A solution of the reduced acetyl compound of ubiquinone-2 (180 mg) and SeO$_2$ (106 mg) in ethanol (8 ml) is heated at 75°–80° C. for 2 hours, at the end of which time the reaction mixture is evaporated to dryness under reduced pressure. The residue is dissolved in CCl$_4$, the insoluble matter is filtered off, the filtrate is evaporated to dryness under reduced pressure and the residue is purified by column chromatography on silica gel (10 g) with CCl$_4$-ethyl acetate (3:1) as the eluent. The procedure yields III$_c$ (R=H$_3$CO, X=Y=OCOCH$_3$, n=1) as colorless oil.

REFERENCE EXAMPLE 5

In a stream of nitrogen gas with stirring at −20° C., a solution of III$_a$ (R, R=

X=Y=OCOCH$_3$, n=O, R$_3$=C$_2$H$_5$) (112 mg) in ether (30 ml) is added to a solution of LiAlH$_4$ (203 mg) in ether (20 ml). After 20 minutes' stirring, cold water is added to the reaction mixture to thereby decompose the excess LiAlH$_4$. This reaction mixture contains III$_b$ (R, R=

$X=Y=OH$, $n=0$, $m=1$).

REFERENCE EXAMPLE 6

Under stirring at −20° C., a solution of ethyl 5-methoxycarbonyl-3-methyl-2-pentenoate (6 g) in ether (60 ml) is added to a solution of LiAlH$_4$ (2.0 g) in ether (100 ml). After 70 minutes' stirring, cold water is added to the reaction mixture to thereby decompose the excess LiAlH$_4$. Then, a saturated aqueous solution of sodium hydrogen carbonate is added, followed by extraction with ethyl acetate. The extract is worked up in the conventional manner and the residue is purified by column chromatography on silica gel (150 g) with chloroform-methanol (15:1) as the eluent. The procedure yields a colorless oil of VII ($R_4=R_5=H$, $n=O$, $m=2$). This product (318 mg) and 2,3-dimethoxy-5-methyl-1,4-benzoquinone (313 mg) are subjected to reduction with Na$_2$S$_2$O$_4$ (3 g) in the conventional manner and the resulting VI ($R=H_3CO$, $X=Y=OH$) is dissolved in dioxane (6 ml), followed by addition of a mixture of BF$_3$-ether (3 ml) and dioxane (6 ml) under stirring at room temperature. The mixture is further stirred for 90 minutes, whereby III$_b$ ($R=H_3CO$, $X=Y=OH$, $n=O$, $m=3$) is produced.

REFERENCE EXAMPLE 7

XIV ($R=H_3CO$, $R_3=CH_3$, $n=O$) (1.49 g) is reduced with Na$_2$S$_2$O$_4$ to obtain XV ($R=H_3CO$, $X=Y=OH$, $n=O$, $R_3=CH_3$) and a solution of this XV in ether (200 ml) is added dropwise to an ethereal solution of LiAlH$_4$ (1 g) under ice-cooling and stirring. The mixture is kept stirred for 3 hours, after which it is worked up in the conventional manner. The above procedure yields III$_b$ ($R=H_3CO$, $X=Y=OH$, $n=O$, $m=3$).

REFERENCE EXAMPLE 8

Under stirring at −78° C., a solution of ethyl 5-methoxycarbonyl-3-methyl-2-pentenoate (3.0 g) in ether (30 ml) is added to a solution of LiAlH$_4$ (1.0 g) in ether (50 ml). The mixture is further, stirred for 30 minutes, after which cold water and a saturated aqueous solution of sodium hydrogen carbonate are added followed by extraction with ethyl acetate. The extract is worked up in the conventional manner and the residue is purified by column chromatography on silica gel (100 g) with CCl$_4$-ethyl acetate (10:1) as the eluent. The above procedure provides a colorless oil of ethyl 6-hydroxy-3-methyl-2-hexenoate. This product (2.6 g) is mixed with 3,4-dihydro-α-pyran (5.2 g) and under ice-cooling, concentrated hydrochloric acid (0.04 ml) is added. The mixture is stirred for 3 hours, after which a saturated aqueous solution of sodium hydrogen carbonate is added followed by extraction with ethyl acetate. The extract is worked up in the conventional manner and the residue is purified by column chromatography on silica gel (100 g) with CCl$_4$-ethyl acetate (10:1) as the eluent. This procedure provides a colorless oil of ethyl 3-methyl-6-(α-tetrahydropyranyloxy)-2-hexenoate. A solution of this product (3.5 g) in ether (50 ml) is added to a solution of LiAlH$_4$ (1.0 g) in ether (100 ml) at −78° C. with constant stirring. The mixture is further stirred at −20° C. for an hour, at the end of which time the excess LiAlH$_4$ is decomposed with cold water. To this reaction mixture is added a saturated aqueous solution of sodium hydrogen carbonate followed by extraction with ethyl acetate. The extract is worked up in the conventional manner and the residue is purified by column chromatography on silica gel (70 g) with CCl$_4$-ethyl acetate (3:1) as the eluent. The above procedure provides a colorless oil of VII ($R_4=H$, $n=O$, $m=2$, $R_5=THP$). This product (1.9 g) and VI ($R=H_3C$, $X=Y=OH$) (2.0 g) are dissolved in dioxane (30 ml), followed by addition of a mixture of BF$_3$-ether (10 ml) and dioxane (20 ml) at room temperature with stirring. The mixture is kept stirred for 2 hours, at the end of which time it is diluted with cold water and extracted with ethyl acetate. The extract is worked up in the conventional manner to recover III$_b$ ($R=H_3C$, $X=Y=OH$, $n=O$, $m=3$).

REFERENCE EXAMPLE 9

To a mixture of VII ($R_4=R_5=H$, $n=O$, $m=3$) (0.785 g) according to Reference Example 6 and 3,4-dihydro-α-pyran (2 ml) is added concentrated hydrochloric acid (0.06 ml) under ice-cooling and stirring. The mixture is kept stirred for 3 hours, at the end of which time a saturated aqueous solution of sodium hydrogen carbonate is added followed by extraction with ethyl acetate. The extract is worked up in the conventional manner and the residue is purified by column chromatography on silica gel (50 g) with CCl$_4$-ethyl acetate (5:1) as the eluent. The above procedure provides a colorless oil of VII ($R_4=R_5=$

$n=O$, $m=3$). This product (1.0 g) and VI ($R=H_3C$, $X=Y=OH$) (1.0 g) are treated together as in Reference Example 8 to obtain III$_b$ ($R=H_3C$, $X=Y=OH$, $n=O$, $m=3$).

REFERENCE EXAMPLE 10

The procedure of Reference Example 8 is repeated using VI (R, $R=$

$X=Y=OH$), which is obtainable on reduction of 2-methyl-1,4-naphthoquinone (240 mg) with Na$_2$S$_2$O$_4$ (2.5 g), and VII ($R_4=R_5=H$, $n=O$, $m=3$) (221 mg). The procedure provides III$_b$ (R, $R=$

$X=Y=OH$, $n=O$, $m=3$).

REFERENCE EXAMPLE 11

An etheral solution of VIII ($R=H_3CO$, $n=O$, $R_3=CH_3$) (1.1 g) is added dropwise to a solution of LiAlH$_4$ (1.06 g) in ether (200 ml) under ice-cooling and stirring and the reaction mixture is worked up in the conventional manner. The above procedure provides III$_e$ (R=H$_3$CO, X=Y=OH, n=O, m=1).

REFERENCE EXAMPLE 12

IX (R=H$_3$C, X=R$_3$=H, n=O, Y=OH) (2 g) is esterified in a methanolic solution of 5N hydrochloric acid (50 ml) to obtain IX (R=H$_3$C, X=H, Y=OH, R$_3$=CH$_3$). This IX is dissolved in ether (40 ml) and the solution is added to an etheral solution of LiAlH$_4$ (400 mg) under ice-cooling and stirring. The mixture is then worked up in the conventional manner and the resulting crystals are recrystallized from ether-hexane. The above procedure yields III$_e$ (R=H$_3$C, X=H, Y=OH, n=O, m=1) as colorless crystals.

REFERENCE EXAMPLE 13

VI (R=H$_3$CO, X=Y=OH), which is obtainable by reducing 2,3-dimethoxy-1,4-benzoquinone (1.4 g) with Na$_2$S$_2$O$_4$ (15 g) in the conventional manner, and 7-formyl-3,7-dimethylhepta-2,6-dienyl-1-ol (X, n=1) (1.44 g) are dissolved in dioxane (50 ml) and a mixture of BF$_3$-ether (4 ml) and dioxane (8 ml) is added to the solution under stirring at room temperature. The mixture is stirred for 90 minutes, whereupon III$_c$ (R=H$_3$CO, X=Y=OH, n=1) is obtained.

REFERENCE EXAMPLE 14

To a solution of NaBH$_4$ (250 mg) in methanol (10 ml) is added a solution of Ic (R=H$_3$CO, n=1) (550 mg) in methanol (10 ml) under ice-cooling and stirring. The mixture is stirred for 15 minutes, whereupon III$_b$ (R=H$_3$CO, X=Y=OH, n=m=1) is obtained.

REFERENCE EXAMPLE 15

To a solution of LiAlH$_4$ (34.3 mg) in ether (4 ml) is added a solution of III$_c$ (R=H$_3$CO, X=Y=OCOCH$_3$, n=1) (86.1 mg) in ether (5 ml) under ice-cooling and stirring. The mixture is stirred for 30 minutes, at the end of which time the excess LiAlH$_4$ is decomposed with cold water and worked up in the conventional manner. The above procedure yields III$_b$ (R=H$_3$CO, X=Y=OH, n=m=1).

REFERENCE EXAMPLE 16

To a solution of geranyl acetate (1.5 g) in CH$_2$Cl$_2$ (30 ml) is added m-chloroperbenzoic acid (1.3 g) under stirring at −20° C. The mixture is stirred for 90 minutes, at the end of which time it is concentrated under reduced pressure and the residue is dissolved in hexane. The insoluble matter is filtered off, the filtrate evaporated to dryness under reduced pressures and the residue purified by column chromatography on silica gel (30 g) with CCl$_4$-ethyl acetate (10:1). The above procedure provides a colorless oil of 1-acetoxy-3-methyl-6,7-epoxy-2-octene. A solution of the above product (780 mg) in ether (10 ml) is added to a solution of LiAlH$_4$ (290 mg) in ether (30 ml) under ice-cooling and stirring. The mixture is stirred for 30 minutes, at the end of which time the excess LiAlH$_4$ is decomposed with cold water. To this reaction mixture is added a saturated aqueous solution of sodium hydrogen carbonate (5 ml), the ether layer is separated, and the water layer is extracted with ethyl acetate. The ether layer and the extract are pooled and worked up in the conventional manner. The residue is purified by column chromatography on silica gel (15 g) with CCl$_4$-acetone (3:1) as the eluent. The procedure yields a colorless oil of 3,7-dimethyl-2-octene-1,7-diol (XI, n=O). 2,3-Dimethoxy-5-methyl-1,4-benzoquinone (336 mg) is reduced with Na$_2$S$_2$O$_4$ (4 g) and the resultant VI (R=H$_3$CO, X=Y=OH) (309 mg) and XI (309 mg) are dissolved in dioxane (10 ml). Under stirring in nitrogen gas stream and at room temperature, a solution of BF$_3$-ether (1.5 ml) in dioxane (2 ml) is added. The mixture is stirred for 2 hours, whereupon III$_d$ (R=H$_3$CO, X=Y=OH, n=O, m=3) is obtained.

REFERENCE EXAMPLE 17

XVI (R=H$_3$CO, n=O, m=3; 1.66 g, 5 mmols), synthesized from ubiquinone-2 by the method of Terao et al (J. Chem. Soc., Perkin Trans. 1, 1978, p. 1101) is dissolved in methanol (20 ml) and the solution is cooled to 5° C. To this solution is added sodium borohydride (200 mg) and the reaction is carried out for 30 minutes. The reaction mixture is evaporated to dryness under reduced pressure, the residue is dissolved in ethyl acetate and the solution is washed with water, dried and evaporated to dryness. The procedure yields crude III$_b$ (R=H$_3$CO, X=Y=OH, m=3, n=O).

REFERENCE EXAMPLE 18

XVI (R=H$_3$CO, n=5, m=3; 1.35 g, 2 mmols), synthesized from ubiquinone-7 by the method of Terao et al (cf. Reference Example 17), is dissolved in methanol and cooled to 5° C. To this solution is added sodium borohydride (80 mg) and the reaction is carried out for 30 minutes. The reaction mixture is then worked up in the same manner as Reference Example 17. The procedure yields crude III$_b$ (R=H$_3$CO, X=Y=OH, m=3, n=5).

REFERENCE EXAMPLE 19

XII (R=H$_3$CO, X=Y=OCH$_2$OCH$_3$, n=2, 4.92 g, 10 mmols), synthesized from ubiquinone-3 by the method described in Japanese Published Unexamined Patent Application No. 50123/1978 (Tokkai Sho No. 53-50123), is dissolved in dry ether (30 ml), followed by addition of lithium aluminum hydride (0.5 g) in a nitrogen gas stream. The mixture is stirred at room temperature for 8 hours. To this reaction mixture is gradually added a saturated aqueous solution of sodium sulfate and the mixture is filtered. The filtrate is evaporated to dryness under reduced pressure and purified by silica gel column chromatography (eluent:isopropyl ether-ethyl acetate=19:1). The above procedure provides III$_d$ (R=H$_3$CO, X=Y=OCH$_2$OCH$_3$, n=1, m=3). 4.44 g (90.3%); NMR δ 1.20(6H), 1.60(3H), 1.78(3H), 2.20(3H), 3.43(2H), 3.60(6H), 3.90(6H), 5.11(4H), 5.1(2H).

REFERENCE EXAMPLE 20

XVI (R=H$_3$CO, n=1, m=3; 3.60 g, 10 mmols), synthesized from ubiquinone-b 3 by the method of Terao et al (cf. Reference Example 17), is dissolved in methanol (20 ml) followed by adddition of sodium borohydride (200 mg) at 0° C. The mixture is stirred for 10 minutes. The reaction mixture is treated with water (100 ml) and extracted with ether. The extract is washed with water, dried and evaporated to dryness under reduced pressure. The procedure yields III$_b$ (R=H$_3$CO, X=Y=OH, n=1, m=3).

REFERENCE EXAMPLE 21

XIII (R=H$_3$CO, X=Y=OCH$_2$OCH$_3$, n=6) (3.82 g, 5 mmols), synthesized from ubiquinone-7 by the method described in Japanese Published Unexamined Patent Application No. 50123/1978 (Tokkai Sho 53-50123), is dissolved in ethyl orthoacetate (30 ml), followed by addition of propionic acid (0.1 ml). The mixture is heated at 140° C. for an hour. The reaction mixture is evaporated to dryness under reduced pressure and the resulting residue is dissolved in ether (50 ml), followed by addition of lithium aluminum hydride (500 mg). The mixture is stirred in a nitrogen gas stream at room temperature for 5 hours. To this reaction mixture is added a saturated aqueous solution of sodium sulfate (5 ml). The mixture is filtered. The ether layer is separated, washed with water, dried and evaporated to dryness under reduced pressure. The above procedure yields III$_b$ (R=H$_3$CO, X=Y=OCH$_2$OCH$_3$, n=6, m=3).

REFERENCE EXAMPLE 22

XIII (R=H$_3$C, X=Y=OCH$_3$, n=1) (3.32 g, 10 mmols), synthesized from 2,3,5-trimethyl-6-geranyl-1,4-benzoquinone by the method described in Japanese Published Unexamined Patent Application No. 50123/1978 (Tokkai Sho No. 53-50123) or J. Chem. Soc. Perkin Trans. 1, 1978, p. 1101, is dissolved in ethyl orthoacetate (30 ml) followed by addition of propionic acid (0.1 ml). The mixture is heated in a nitrogen gas stream at 140° C. for an hour and the by-product ethanol is distilled off. The reaction mixture is evaporated to dryness under reduced pressure and the residue is purified by column chromatography (silica gel 50 g, eluent-:hexane-ether (9:1)), whereby XV (R=H$_3$C, X=Y=OCH$_3$, n=1, R$_3$=C$_2$H$_5$) is obtained. 3.82 g (91.8%). This product (1.6 g, 3.9 mmols) is dissolved in dry ether (40 ml) followed by dropwise addition of methylmagnesium iodide (Mg 2.4 g/ether 40 ml) (5 ml). The mixture is refluxed at 50° C. for 30 minutes. After cooling, the reaction mixture is poured into dilute hydrochloric acid (50 ml) and extraced with ether. This extract is worked up in the conventional manner and the residue is purified by column chromatography (silica gel 30 g, eluent:methylene chloride-ethyl acetate (19:1)). The above procedure provides III$_d$ (R=H$_3$C, X=Y=OCH$_3$, n=1, m=2). 1.5 g (96%). NMR δ 1.14(6H), 1.59(3H), 1.77(3H), 2.20(9H), 3.38(2H), 3.63(6H), 4.8–5.2(2H),

REFERENCE EXAMPLE 23

XIII (R, R=

X=Y=OCH$_3$, n=1) (3.10 g, 8.6 mmols), synthesized from 2-methyl-3-geranyl-1,4-naphthoquinone by the method described in Reference Example 22, is dissolved in ethyl orthoacetate (20 ml) followed by addition of propionic acid (0.1 ml). Thereafter, the mixture is worked up in the same manner as Reference Example 22, whereby XV (R, R=

X=Y=OCH$_3$, n=1, R$_3$=C$_2$H$_5$) is obtained. 2.95 g (77%). NMR δ 1.22(3H), 1.54(3H), 1.84(3H), 2.38(3H), 3.56(2H), 3.85(6H), 4.08(2H), 4.96–5.23(2H), 7.22–7.56(2H), 7.86–8.14(2H).

This product (2.5 g, 5.7 mmols) is dissolved in dry ether (30 ml) followed by addition of methyl Grignard reagent. After this reaction, the reaction mixture is worked up in the conventional manner to obtain III$_d$ (R, R=

X=Y=OCH$_3$, n=1, m=2). 2.3 g (95%). NMR δ 1.20(6H), 1.60(3H), 1.86(3H), 2.36(3H), 3.57(2H), 3.88(6H), 4.89–5.24(2H), 7.26–8.58(2H), 7.83–8.18(2H).

REFERENCE EXAMPLE 24

XIII (R=H$_3$CO, X=Y=OCH$_2$OCH$_3$, n=1), synthesized from ubiquinone-2 by the method described in Japanese Published Unexamined Patent Application No. 50123/1978 (Tokkai Sho No. 53-50123), is dissolved in ethyl orthoacetate (30 ml) followed by addition of propionic acid (0.1 ml). The reaction is carried out at 140° C. for an hour and the reaction mixture is worked up in the conventional manner to obtain XV (R=H$_3$CO, X=Y=OCH$_2$OCH$_3$, n=1, R$_3$=C$_2$H$_5$). 4.31 g (87.2%). NMR δ 1.20(3H), 1.58(3H), 1.78(3H), 2.05(CH$_2$), 2.20(3H), 2.34(2H), 3.46(2H), 3.58(6H), 3.88(6H), 4.16(2H), 5.11(4H), 5.2(2H).

This product (1.48 g, 3 mmols) is dissolved in ether (20 ml) followed by addition of methyl Grignard reagent. Thereafter, the mixture is worked up in the same manner as Reference Example 22 to obtain III$_d$ (R=H$_3$CO, X=Y=OCH$_2$OCH$_3$, n=1, m=2). 1.32 g (92%). NMR δ 1.20(3H), 1.22(6H), 1.58(3H), 1.73(3H), 2.05(CH$_2$), 2.20(3H), 3.45(2H), 3.58(6H), 3.88(6H), 5.11(4H), 5.2(2H).

EXAMPLE 1

To a solution of III$_a$ (R=H$_3$CO, X=Y=OCOCH$_3$, n=O, R$_3$=C$_2$H$_5$) (680 mg) and Na$_2$S$_2$O$_4$ (2.1 g) in acetone (7 ml) is added 10% KOH (30 ml) under stirring in a nitrogen gas stream at room temperature. The mixture is stirred for 30 minutes, and after cold water is added, is neutralized with cold 3N HCl (20 ml) and extracted with ethyl acetate. The extract is worked up in the conventional manner and the residue is dissolved in 83% methanol (36 ml), followed by addition of a solution of FeCl$_3$ (35 g) in 83% methanol (48 ml) under stirring at room temperature. The mixture is stirred for 90 minutes, at the end of which time cold water is added, followed by extraction with ethyl acetate. The extract is worked up in the conventional manner and the residue is purified by column chromatography on silica gel (30 g) with CCl$_4$-ethyl acetate-acetic acid (100:30:1) as the eluent. The first-emerging fraction is recrystallized from benzene-hexane to obtain I$_a$ (R=H$_3$CO, n=O) as orange-colored needles. m.p. 118.5°–119.5° C. Elemental analysis: calcd. for C$_{14}$H$_{16}$O$_6$—c, 59.99; H, 5.75; found—C, 60.13; H, 5.62. The second-emerging fraction is treated in the conventional manner to obtain an orange-red oil which is then purified by thin-layer chromatography on silica gel with CCl$_4$-acetone-acetic acid (50:25:1) as the developing solvent. The procedure provides an orange red oil of If (R=H$_3$CO, n=0). Elemental analysis: calcd. for C$_{14}$H$_{18}$O$_7$—C, 56.37; H, 6.08; found—C, 56.19; H, 6.43.

EXAMPLE 2

III$_a$ (R=H$_3$C, X=Y=OCOCH$_3$, n=0, R$_3$=C$_2$H$_5$) (1.2 g) is treated in the same manner as Example 1 to obtain I$_d$ (R=H$_3$C, n=0) as yellow needles, m.p. 149°-152° C. Elemental analysis: calcd. for C$_{14}$H$_{16}$O$_4$—C, 67.73; H, 6.50; found—C, 67.39; H, 6.44. Then, I$_f$ (R=H$_3$C, n=0) is obtained as yellow needles, m.p. 106°-110° C. Elemental analysis: calcd. for C$_{14}$H$_{18}$O$_5$—C, 63.14; H, 6.81; found—C, 63.08; H, 6.87.

EXAMPLE 3

III$_a$ (R, R=

X=Y=OCOCH$_3$, n=0, R$_3$=C$_2$H$_5$) (1.6 g) is treated in the same manner as Example 1 to obtain I$_a$ (R, R=

n=0) as yellow needles, m.p. 165°-167° C. (decomp.) Elemental analysis: calcd. for C$_{16}$H$_{14}$O$_4$—C, 71.10; H, 5.22; found—C, 71.15; H, 5.00. Then, as a second product, I$_f$ (R, R=

n=0) is obtained as yellow needles, m.p. 144.5°-150.5° C. Elemental analysis: calcd. for C$_{16}$H$_{16}$O$_5$—C, 66.66; H, 5.59; found—C, 66.64; H, 5.58.

EXAMPLE 4

To the reaction mixture containing III$_b$ (R=H$_3$C, X=Y=OH, n=0, m=1) obtained in Reference Example 2 is added a solution of FeCl$_3$ (8 g) in 83% methanol (24 ml) with stirring at room temperature. The mixture is further stirred for 30 minutes, at the end of which time it is treated with cold water and extracted with ethyl acetate. The extract is worked up in the conventional manner and the residue is purified by column chromatography on silica gel (20 g) with CCl$_4$-acetone (10:1) as the eluent. The above procedure yields a yellow oil of I$_b$ (R=H$_3$C, n=0, m=1). NMR (CDCl$_3$) δ: 1.26(1H, OH), 1.80(3H, side chain methyl), 2.02(9H, nuclear methyl), 3.25(2H, CH$_2$CH=), 3.98(2H, CH$_2$OH), 5.26(1H, CH$_2$CH=), Mass spectrum (C$_{14}$H$_{18}$O$_3$=234.28)m/e: 234(M+).

EXAMPLE 5

To the reaction mixture containing III$_b$ (R, R=

X=Y=OH, m=0, m=1) obtained in Reference Example 5 is added a solution of FeCl$_3$ (10 g) in water (70 ml). The mixture is stirred at room temperature for 30 minutes, at the end of which time it is treated with cold water and extracted with ethyl acetate. The extract is worked up in the conventional manner and the residue is purified by column chromatography on silica gel (5 g) with CCl$_4$-ethyl acetate (5:1) as the eluent and further by thin-layer chromatography using CCl$_4$-ethyl acetate (5:1) as the developing solvent system. The above procedure provide I$_b$ (R, R=

n=0, m=1) as yellow oil. NMR (CDCl$_3$) δ: 1.66(1H, OH), 1.85(3H, side chain methyl), 2.20(3H, nuclear CH$_3$), 3.41(2H, CH$_2$CH=), 4.00(2H, CH$_2$OH), 5.34(1H, CH$_2$CH=), 7.5-8.2(4H, nuclear protons). Mass spectrum (C$_{16}$H$_{16}$O$_3$=256.29)m/e: 256(M+).

EXAMPLE 6

To the reaction mixture containing III$_b$ (R=H$_3$CO, X=Y=OH, n=0, m=3) obtained in Reference Example 7 is added a solution of FeCl$_3$ (3 g) in 83% methanol (18 ml). The mixture is stirred for 30 minutes, at the end of which time it is treated with cold water and extracted with ethyl acetate. The extracted is worked up in the conventional manner and the residue is purified by column chromatography on silica gel (20 g) with CCl$_4$-ethyl acetate (3:1) as the eluent and, then, by thin-layer chromatography on silica gel with CCl$_4$-ethyl acetate (3:1) as the developing solvent. The above procedure yields I$_b$ (R=H$_3$CO, n=0, m=3) as orange-colored oil. Elemental analysis: calcd. for C$_{19}$H$_{22}$O$_5$—C, 65.29; H, 7.53; found—C, 64.99; H, 7.62.

EXAMPLE 7

To a solution of III$_b$ (R=H$_3$C, X=Y=OH, n=0, m=3) obtained in Reference Example 8 or 9 in 83% methanol (48 ml) is added a solution of FeCl$_3$ (20 g) in methanol (48 ml) under stirring at room temperature. The mixture is stirred for 30 minutes, at the end of which time it is treated with cold water and extracted with ethyl acetate. The extract is purified in the same manner as Example 6 to obtain I$_b$ (R=H$_3$C, n=0, m=3) as yellow oil. Elemental analysis: calcd. for C$_{16}$H$_{22}$O$_3$—C, 73.25; H, 8.45; found C, 72.73; H, 8.54.

EXAMPLE 8

III$_b$ (R, R=

X=Y=OH, n=0, m=3) as obtained in Reference Example 10 is treated in the same manner as Example 6 to obtain I$_b$ (R, R=

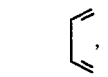

n=0, m=3) as a yellow oil. Elemental analysis: calcd. for C$_{18}$H$_{20}$O$_3$—C, 76.03; H, 7.09; found—C, 75.93; H, 7.29.

EXAMPLE 9

III$_e$ (R=H$_3$CO, X=Y=OH, n=0, m=1) as obtained in Reference Example 11 is oxidized with FeCl$_3$ (10 g) and purified by column chromatography on silica gel (30 g) with CHCl$_3$ as the eluent. This procedure yields I$_e$ (R=H$_3$CO, n=0, m=1) as orange-yellow oil. Elemental analysis: calcd. for C$_{14}$H$_{20}$O$_5$—C, 62.67; H, 7.51; found—C, 67.69; H, 7.57.

EXAMPLE 10

To a solution of III$_e$ (R=H$_3$C, X=H, Y=OH, n=0, m=1) (1.237 g) obtained in Reference Example 12 in acetone (20 ml) is added a solution of ON(SO$_3$K)$_2$ (12.5 g) in water (200 ml) and 0.17M KH$_2$PO$_4$ (15 ml), and the mixture is stirred at room temperature for 2 hours. The reaction mixture is extracted with ethyl acetate, the extract is treated in the conventional manner and the residue is purified by column chromatograpy on silica gel (30 g) with CHCl$_3$ as the eluent. The procedure yields I$_e$ (R=H$_3$C, n=0, m=1) as yellow oil. Elemental analysis: calcd. for C$_{14}$H$_{20}$O$_3$—C, 71.16; H, 8.53; found—C, 71.24; H, 8.57.

EXAMPLE 11

To the reaction mixture of III$_c$ (R=H$_3$CO, X=Y=OH, n=1) obtained in Reference Example 13 is added a solution of FeCl$_3$ (15 g) in 83% methanol (36 ml). The mixture is stirred for 15 minutes, at the end of which time it is treated with cold water and extracted with ethyl acetate. The extract is worked up in the conventional manner and the residue is purified by column chromatography on silica gel (75 g) with benzene as the eluent. The above procedure yields I$_c$ (R=H$_3$CO, n=1) as orange-colored oil. Elemental analysis: calcd. for C$_{19}$H$_{24}$O$_5$—C, 63.65; H, 7.28; found—C, 68.70; H, 7.19.

EXAMPLE 12

To the reaction mixture containing III$_b$ (R=H$_3$CO, X=Y=OH, m=n=1) obtained in Reference Example 14 is added a solution of FeCl$_3$ (5.0 g) in 83% methanol (24 ml) under ice-cooling and stirring. The mixture is stirred for 15 minutes, at the end of which time it is treated with cold water and extracted with ethyl acetate. The extract is worked up in the conventional manner and the residue is purified by column chromatography on silica gel (30 g) with CCl$_4$-ethyl acetate (3:1) as the eluent. The above procedure yields I$_b$ (R=H$_3$CO, m=n=1) as orange-colored oil. Elemental analysis: calcd. for C$_{19}$H$_{26}$O$_5$—C, 68.24; H, 7.84; found—C, 68.07; H, 7.82.

EXAMPLE 13

To the reaction mixture containing III$_b$ (R=H$_3$CO, X=Y=OH, m=n=1) obtained in Reference Example 15 is added a solution of FeCl$_3$ (0.8 g) in water (10 ml) under ice-cooling and stirring. The mixture is stirred for 30 minutes, at the end of which time it is treated with cold water and extracted with ethyl acetate. The extract is worked up in the conventional manner and the residue is purified by column chromatography on silica gel (8 g) with CCl$_4$-acetone (10:1) as the eluent. The above procedure yields I$_b$ (R=H$_3$CO, m=n=1) as orange-colored oil.

EXAMPLE 14

To the reaction mixture containing III$_d$ (R=H$_3$CO, X=Y=OH, m=3, n=0) obtained in Reference Example 16 is added a solution of FeCl$_3$ (4 g) in 83% methanol (24 ml) under stirring at room temperature. The mixture is stirred for 15 minutes, at the end of which time it is treated with cold water and extracted with ethyl acetate. The extract is worked up in the conventional manner and purified by column chromatography on silica gel (15 g) with CCl$_4$-ethyl acetate (5:1) as the eluent. The above procedure yields I$_d$ (R=H$_3$CO, m=3, n=0) as orange-colored oil. Elemental analysis: calcd. for C$_{19}$H$_{28}$O$_5$—C, 67.83; H, 8.39; found—C, 67.97; H, 8.39.

EXAMPLE 15

A solution of III$_b$ (R=H$_3$CO, X=Y=OCOCH$_3$, m=1, n=2) (86 mg) obtained in Reference Example 3 in ether (5 ml) is added to a solution of LiAlH$_4$ (34 mg) in ether (4 ml) under ice-cooling and stirring. The mixture is stirred for 30 minutes, at the end of which time the excess LiAlH$_4$ is decomposed with cold water. To this reaction mixture is added a solution of FeCl$_3$ (0.8 g) in water (10 ml), followed by extraction with ethyl acetate. The extract is worked up in the conventional manner and the residue is purified by column chromatography on silica gel (8 g) with CCl$_4$-acetone (10:1) as the eluent. The above procedure yields I$_b$ (R=H$_3$CO, n=2, m=1) as orange-colored oil. NMR (CDCl$_3$) δ: 1.66, 1.73(s, 9H, side chain methyl), 1.8-2.3 (m, 8H, side chain methylene), 2.02 s, 3H, nuclear methyl), 3.17(d, 2H, methylene adjacent to nucleus), 3.98(s, 6H, nuclear methoxy), 3.98(s, 2H, methylene adjacent to 0), 4.7-5.55 (m, 3H, vinyl protons).

EXAMPLE 16

To the crude III$_b$ (X=Y=OH, R=H$_3$CO, n=0, m=3) according to Reference Example 17 are added ether (10 ml) and at 16.4% of aqueous solution of ferric chloride (10 ml), followed by stirring at room temperature for 30 minutes. The ether layer is washed with water, dried and evaporated under reduced pressure. The residue is purified by column chromatography [silica gel 30 g; eluent: isopropyl ether-ethyl acetyl (4:1)] to obtain I$_b$ (R=H$_3$CO, m=3, n=0), 1.48 g (88.6%). NMR δ 1.63(3H), 1.68(3H), 3.18(2H), 3.84(2H), 3.97(3H), 3.99(3H), 5.2-5.3(2H).

EXAMPLE 17

The crude III$_b$ (R=H$_3$CO, X=Y=OH, n=5, m=3) according to Reference Example 18 is treated in the same manner as Example 16 except that a 9:1 mixture of isopropyl ether-ethyl acetate is employed. The procedure yields I$_b$ (R=H$_3$CO, m=3, n=5). 1.26 g (92.6%). NMR δ 1.61(18H), 1.68(3H), 3.18(2H), 3.84(2H), 3.97(3H), 3.99(3H), 5.1(7H).

EXAMPLE 18

The III$_d$ (R=H$_3$CO, X=Y=OCH$_2$OCH$_3$, n=1, m=3) (3.44 g, 7 mmols) obtained in Reference Example 19 is dissolved in a mixture of acetone (20 ml) and 10% sulfuric acid (5 ml), and the solution is warmed at 45° C. for 8 hours. After cooling, a 16.4% aqueous solution of ferric chloride (15 ml) is added to the reaction mixture, followed by stirring for 30 minutes. The mixture is extracted three times with ether (50 ml portions) and the extract is washed with water, dried and evaporated to dryness under reduced pressure. The residue is purified to column chromatography under the same conditions as described in Reference Example 19. The above procedure yields $I_d$ (R=H$_3$CO, n=1, m=3). 2.2 g (78.5%), NMR δ 1.20(6H), 1.60(3H), 1.76(3H), 2.0(CH$_3$, CH$_2$), 3.24(2H), 4.00(6H), 5.2(2H).

EXAMPLE 19

To the III$_b$ (R=H$_3$CO, X=Y=OH, n=1, m=3) according to Reference Example 20 are added ether (10 ml) and a 16.4% aqueous solution of ferric chloride (20 ml), and the mixture is stirred for 30 minutes. This reaction mixture is thereafter treated in the same manner as Example 16 except that a 9:1 mixture of isopropyl ether-ethyl acetate is used as the eluent. The above procedure yields $I_b$ (R=H$_3$CO, n=1, m=3). 3.0 g (83.3%). NMR δ 1.67(3H), 1.76(3H), 3.24(3H), 3.5(2H), 4.0(6H), 5.10(2H).

EXAMPLE 20

The III$_b$ (R=H$_3$CO, X=Y=OH, n=5, m=3) (1.64 g, 2 mmols) prepared from ubiquinone-7 by the same procedure as Reference Example 20 is treated as in Example 19 to obtain $I_b$ (R=H$_3$CO, n=5, m=3). 1.54 g (91%). NMR δ 1.60 (15H), 1.74(3H), 2.0(CH$_2$), 3.24(2H), 3.5(2H), 4.0(6H), 5.1(6H).

EXAMPLE 21

The III$_b$ (R=H$_3$CO, X=Y=OCH$_2$OCH$_3$, n=6, m=3) obtained in Reference Example 21 is dissolved in acetone (20 ml) followed by addition of 10% sulfuric acid (5 ml). The mixture is reacted at 40° C. for 10 hours. After cooling, 16.4% aqueous solution of ferric chloride (10 ml) is added and the mixture is stirred for 30 minutes. Thereafter the reaction mixture is worked up in the conventional manner and the residue is purified by column chromatography on silica gel [eluent: isopropyl ether-ethyl acetate (97:3)]. The procedure yields $I_b$ (R=H$_3$CO, n=6, m=3). 2.1 g (59.8%). NMR δ 1.60(18H), 1.74(3H), 2.0(CH$_2$), 3.24(2H), 3.5(2H), 4.0(6H), 5.1(7H).

EXAMPLE 22

The III$_d$ (R=H$_3$C, X=Y=OCH$_3$, n=1, m=2) (1.16 g, 3 mmols) obtained in Reference Example 22 is dissolved in a mixture of dioxane (10 ml) and ether (10 ml) followed by cooling to −15° C. Silver (II) oxide (AgO, 1.0 g) and, then, 6.4N nitric acid (1.3 ml) are added and the mixture is stirred at −10° C. for 10 minutes. After this reaction, hexane (50 ml) and water (10 ml) are added. The organic layer is taken and treated in the conventional manner, and the residue is purified by column chromatography (silica gel 20 g, eluent: isopropyl ether) to obtain $I_d$ (R=H$_3$C, n=1, m=2). 820 mg. NMR δ 1.21(6H), 1.63(3H), 1.80(3H), 2.03(9H), 3.24(2H), 5.1(2H).

EXAMPLE 23

The III$_d$ (R, =

X=Y=OCH$_3$, n=1, m=2) (2.12 g, 15 mmols) obtained in Reference Example 23 is dissolved in a mixture of dioxane (15 ml) and ether (15 ml). The solution is cooled to −15° C., and silver (II) oxide (AgO) (1.7 g) and, then, 6.4N nitric acid (2.2 ml) are added to the solution. The mixture is stirred at −10° C. for 10 minutes, at the end of which time it is treated in the same manner as Example 22. The above procedure yields $I_d$ (R, R=

n=1, m=2). 1.53 g (80.5%). NMR δ 1.21(6H), 1.59(3H), 1.80(3H), 2.35(3H), 3.38(2H), 5.1(2H), 7.6-8.2(4H).

EXAMPLE 24

The III$_d$ (R=H$_3$CO, X=Y=OCH$_2$OCH$_3$, n=1, m=2) (1.3 g) obtained in Reference Example 24 is dissolved in acetone (10 ml) followed by addition of 3N sulfuric acid (5 ml). The mixture is reacted at 45° C. for 8 hours, at the end of which time it is extracted with ether. The ether layer is washed with water and, then, 16.4% aqueous solution of ferric chloride (8 ml) is added. Thereafter, the mixture is treated in the conventional manner to obtain $I_d$ (R=H$_3$CO, n=1, m=2). 868 mg. NMR δ 1.21(6H), 1.60(3H), 1.75(3H), 1.98(CH$_2$.CH$_3$), 3.95(6H), 4.8-5.3(2H).

What is claimed is:

1. A compound of the formula:

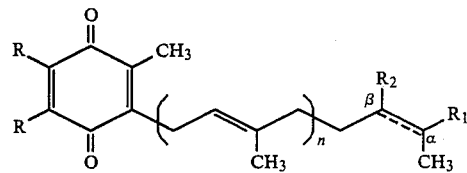

wherein α====β is a saturated bond or a double bond; each R independently of one another is methyl or methoxy, or the two R groups taken together represent —CH=CH—CH=CH—; when α====β is a saturated bond, R$_2$ is hydrogen or hydroxyl; when α====β is a double bond, R$_2$ is hydrogen; when α====β is a double bond or when R$_2$ is hydroxyl, R$_1$ is carboxyl, (CH$_2$)$_m$OH wherein m is an integer of 1 through 3, or

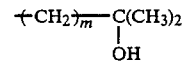

wherein m is an integer of 1 through 3; when α====β is a saturated bond and R$_2$ is hydrogen, R$_1$ is hydroxymethyl or

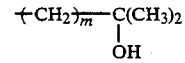

wherein m is an integer of 1 through 3; and n is zero or an integer of 1 through 9, provided that when α====β is a double bond and at the same time R$_1$ is (CH$_2$)$_m$OH, n is an integer of 1 through 9, and provided that when α====β is a saturated bond and at the same time R$_2$ is hydrogen and at the same time R$_1$ is CH$_2$OH, each R independently of one another is methyl or methoxy, and provided that when α====β is a double bond and at the same time R$_1$ is COOH, n is an integer of 1 through 5 or 7 through 9, or a pharmaceutically acceptable salt thereof.

2. A compound according to claim 1, wherein α β is a double bond and $R_1$ is carboxyl.

3. A compound according to claim 1, wherein $R_1$ is carboxyl and $R_2$ is hydroxyl.

4. A compound according to claim 2 or 3, wherein n is zero.

5. A compound according to claim 1, wherein α====β is a double bond and $R_1$ is $-(CH_2)_m OH$ where m is an integer of 1 through 3.

6. A compound according to claim 5, wherein m is 3.

7. A compound according to claim 6, wherein n is an integer of 1 through 6.

8. A compound according to claim 7, wherein n is an integer of 1 or 2.

9. A compound according to claim 5, wherein n is an integer of 1 through 9 and m is 1.

10. A compound according to claim 1, wherein α====β is a saturated bond, $R_1$ is $-CH_2OH$ and $R_2$ is hydrogen.

11. A compound according to claim 10, wherein n is zero.

12. A compound according to claim 1, wherein α====β is a double bond and $R_1$ is

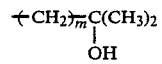

where m is an integer of 1 through 3.

13. A compound according to claim 12, wherein m is 2 or 3.

14. A compound according to claim 1, wherein each R is methoxy.

* * * * *